(12) United States Patent
Muto et al.

(10) Patent No.: US 7,758,586 B2
(45) Date of Patent: Jul. 20, 2010

(54) METHOD AND APPARATUS FOR INTRODUCING CATHETERS

(75) Inventors: Rudolph Muto, Lawrence, MA (US); Nicholas Want, Manchester, NH (US); Jeffrey P. McGill, Northborough, MA (US)

(73) Assignee: Atrium Medical Corporation, Hudson, NH (US)

( * ) Notice: Subject to any disclaimer, the term of this patent is extended or adjusted under 35 U.S.C. 154(b) by 1418 days.

(21) Appl. No.: 10/428,981

(22) Filed: May 2, 2003

(65) Prior Publication Data

US 2004/0220584 A1    Nov. 4, 2004

(51) Int. Cl.
*A61F 11/00* (2006.01)

(52) U.S. Cl. .............. 606/108; 600/201; 600/217; 604/164.01; 604/164.12; 81/3.55; 81/3.57

(58) Field of Classification Search .............. 606/108; 433/3–4, 141–143, 148, 152, 164; 604/164.01, 604/164.12, 171; 600/201, 210, 217; 81/3.41, 81/3.55, 3.57
See application file for complete search history.

(56) References Cited

U.S. PATENT DOCUMENTS

| | | | | | |
|---|---|---|---|---|---|
| 886,987 | A | * | 5/1908 | Kiehle | ........................... 7/144 |
| 985,755 | A | * | 2/1911 | Gilbert | ...................... 294/99.2 |
| D162,082 | S | * | 2/1951 | Preis et al. | ...................... D8/18 |
| 2,716,277 | A | * | 8/1955 | Riley | ........................... 30/450 |
| 2,964,763 | A | * | 12/1960 | Nagy et al. | ...................... 7/152 |
| 3,367,336 | A | * | 2/1968 | Eizenberg | ................... 606/210 |
| 3,392,727 | A | * | 7/1968 | Hanlon | ........................ 606/210 |
| 3,528,427 | A | | 9/1970 | Sheridan et al. | |
| 3,584,624 | A | | 6/1971 | Clutlis | |
| 3,653,389 | A | * | 4/1972 | Shannon | ..................... 606/210 |
| 3,656,375 | A | * | 4/1972 | Reed et al. | ..................... 81/3.55 |
| 3,757,368 | A | * | 9/1973 | Thompson | ...................... 7/142 |
| 3,788,328 | A | | 1/1974 | Alley et al. | |
| 3,903,895 | A | | 9/1975 | Alley et al. | |
| D247,263 | S | * | 2/1978 | Van Benthem | ............... D3/210 |
| 4,135,267 | A | * | 1/1979 | McKinney et al. | .............. 7/151 |
| 4,207,781 | A | * | 6/1980 | Greenwood | .................. 81/3.55 |
| 4,359,053 | A | | 11/1982 | Benjamin | |
| 4,431,426 | A | | 2/1984 | Groshong et al. | |
| 4,432,752 | A | | 2/1984 | Marlon | |
| 4,453,928 | A | | 6/1984 | Steiger | |
| 4,478,221 | A | * | 10/1984 | Heiss | .......................... 606/145 |
| 4,484,911 | A | * | 11/1984 | Berlin et al. | ................. 604/174 |
| 4,490,136 | A | | 12/1984 | Ekbladh et al. | |
| 4,504,269 | A | | 3/1985 | Durand | |
| 4,608,982 | A | * | 9/1986 | Pollard | ........................ 606/190 |
| 4,617,842 | A | * | 10/1986 | Yang | ........................... 81/3.09 |
| 4,631,769 | A | * | 12/1986 | White | ............................ 7/151 |
| 4,692,154 | A | | 9/1987 | Singery et al. | |
| 4,830,222 | A | * | 5/1989 | Read | ........................... 222/106 |

(Continued)

*Primary Examiner*—Nicholas D Lucchesi
*Assistant Examiner*—Quynh-Nhu H Vu
(74) *Attorney, Agent, or Firm*—RatnerPrestia

(57) ABSTRACT

An apparatus is provided for introducing a catheter through a body opening along an insertion axis. The apparatus includes an arm having an end portion configured to extend into the body opening along the insertion axis, wherein the arm is configured to extend adjacent an external catheter surface. The apparatus also includes a surface extending from the end portion of the arm at an angle to the insertion axis, wherein the surface is configured to extend at least partially within an aperture formed in the catheter.

7 Claims, 14 Drawing Sheets

U.S. PATENT DOCUMENTS

| | | |
|---|---|---|
| 4,883,474 A | 11/1989 | Sheridan et al. |
| D322,201 S * | 12/1991 | Rokita .......................... D8/18 |
| 5,205,830 A | 4/1993 | Dassa et al. |
| 5,250,075 A * | 10/1993 | Badie ......................... 606/207 |
| 5,613,956 A | 3/1997 | Patterson et al. |
| 5,772,670 A * | 6/1998 | Brosa .......................... 606/108 |
| 5,855,590 A | 1/1999 | Malecki et al. |
| 6,220,118 B1 * | 4/2001 | Pacheco et al. ............... 81/3.55 |
| 6,447,522 B2 | 9/2002 | Gambale et al. |
| 6,478,776 B1 | 11/2002 | Rosenman et al. |
| 6,494,211 B1 | 12/2002 | Boyd et al. |
| 6,530,914 B1 | 3/2003 | Mickley |
| D495,570 S * | 9/2004 | Kelleghan ..................... D8/38 |
| 6,929,606 B2 * | 8/2005 | Ritland ........................ 600/201 |
| D513,575 S * | 1/2006 | Carson et al. .................. D8/16 |
| 2002/0127514 A1 * | 9/2002 | Dietrich ....................... 433/159 |

\* cited by examiner

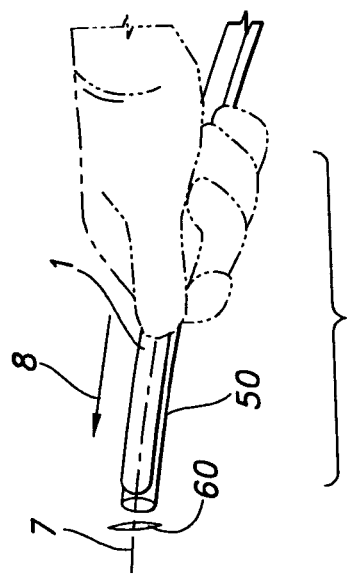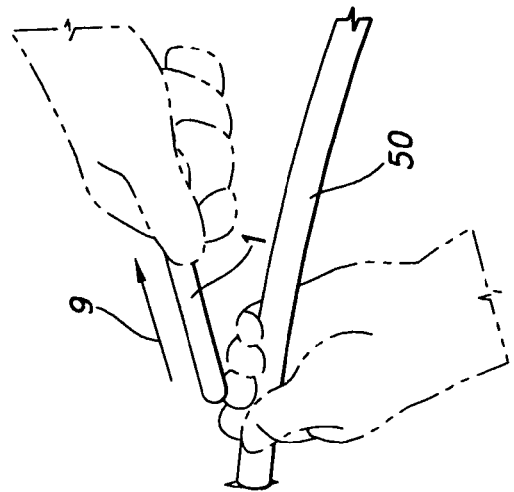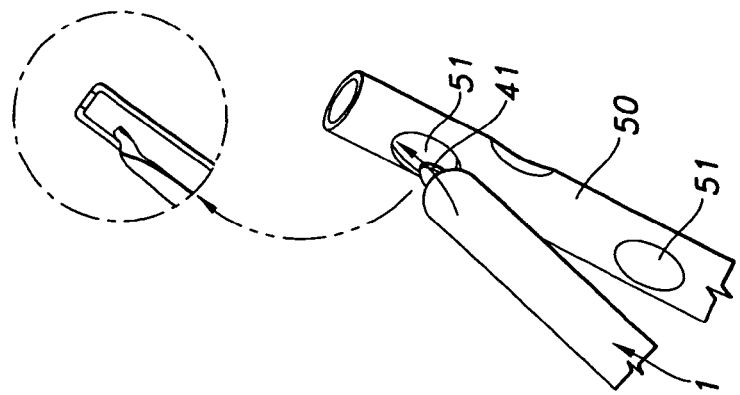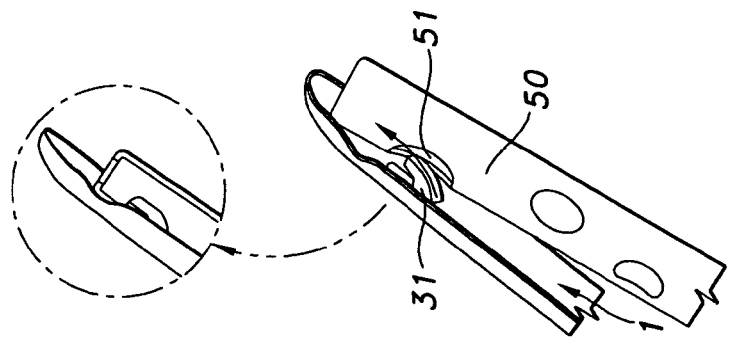

US 7,758,586 B2

METHOD AND APPARATUS FOR INTRODUCING CATHETERS

FIELD OF THE INVENTION

This invention relates generally to an apparatus for introducing a catheter and a method for its use, and more particularly to an apparatus for introducing a drainage catheter through a body opening.

BACKGROUND OF THE INVENTION

Catheters often need to be inserted or pushed through a body opening, such as an incision or a body orifice, during a surgical or other medical procedure. Such catheters may be useful for a variety of purposes, including the drainage of bodily fluids from a surgical patient or a patient undergoing medical treatment. For example, thoracic drainage catheters, such as those that are introduced into a body opening outside of the operating room environment, require that the catheter be pushed through tissue and between rib structures to be properly positioned in the pleural space. Such positioning may need to be accomplished without the benefit of the chest being open to aid in positioning.

Catheters are typically "soft" and "flexible" by design to conform to internal structures and anatomy. For example, thoracic drainage catheters may be formed from silicone or other very soft plastic materials. Thus, it is sometimes difficult to push the tip of a catheter through a body opening in such a way as to avoid buckling of the catheter.

Accordingly, there is a need for an apparatus and method for introducing catheters, such as thoracic drainage catheters, into a body opening in such a way as to reduce the tendency of the catheter to buckle.

SUMMARY OF THE INVENTION

An apparatus is provided for introducing a catheter through a body opening along an insertion axis. The apparatus includes an arm having an end portion configured to extend into the body opening along the insertion axis, wherein the arm is configured to extend adjacent an external catheter surface. The apparatus also includes a surface extending from the end portion of the arm at an angle to the insertion axis, wherein the surface is configured to extend at least partially within an aperture formed in the catheter.

A method for introducing a catheter into a body opening is also provided. The method includes inserting a surface of an introducer at least partially within an aperture formed in an end portion of a catheter, thereby engaging the catheter. The method also includes advancing the introducer into the body opening, thereby applying tension to the catheter to introduce the catheter at least partially into the body opening.

BRIEF DESCRIPTION OF THE DRAWINGS

The invention is best understood from the following detailed description when read in connection with the accompanying drawing. It is emphasized that, according to common practice, the various features of the drawing are not rendered to any particular proportion or scale. On the contrary, the dimensions of the various features are arbitrarily expanded or reduced for clarity. Included in the drawing are the following figures:

FIG. 10A shows an exemplary embodiment of an apparatus for introducing a catheter into a body opening being attached at its first end portion to an aperture formed in a catheter to form a catheter system according to aspects of the invention;

FIG. 10B shows an exemplary embodiment of an apparatus for introducing a catheter into a body opening being attached at its second end portion to an aperture formed in a catheter to form a catheter system according to aspects of the invention;

FIG. 11 shows an exemplary catheter system being inserted into a body opening according to aspects of the invention;

FIG. 12 shows an exemplary apparatus for introducing a catheter into a body opening being withdrawn from the body opening, while a catheter remains in the body opening according to aspects of the present invention;

DETAILED DESCRIPTION OF THE INVENTION

Figure 1:
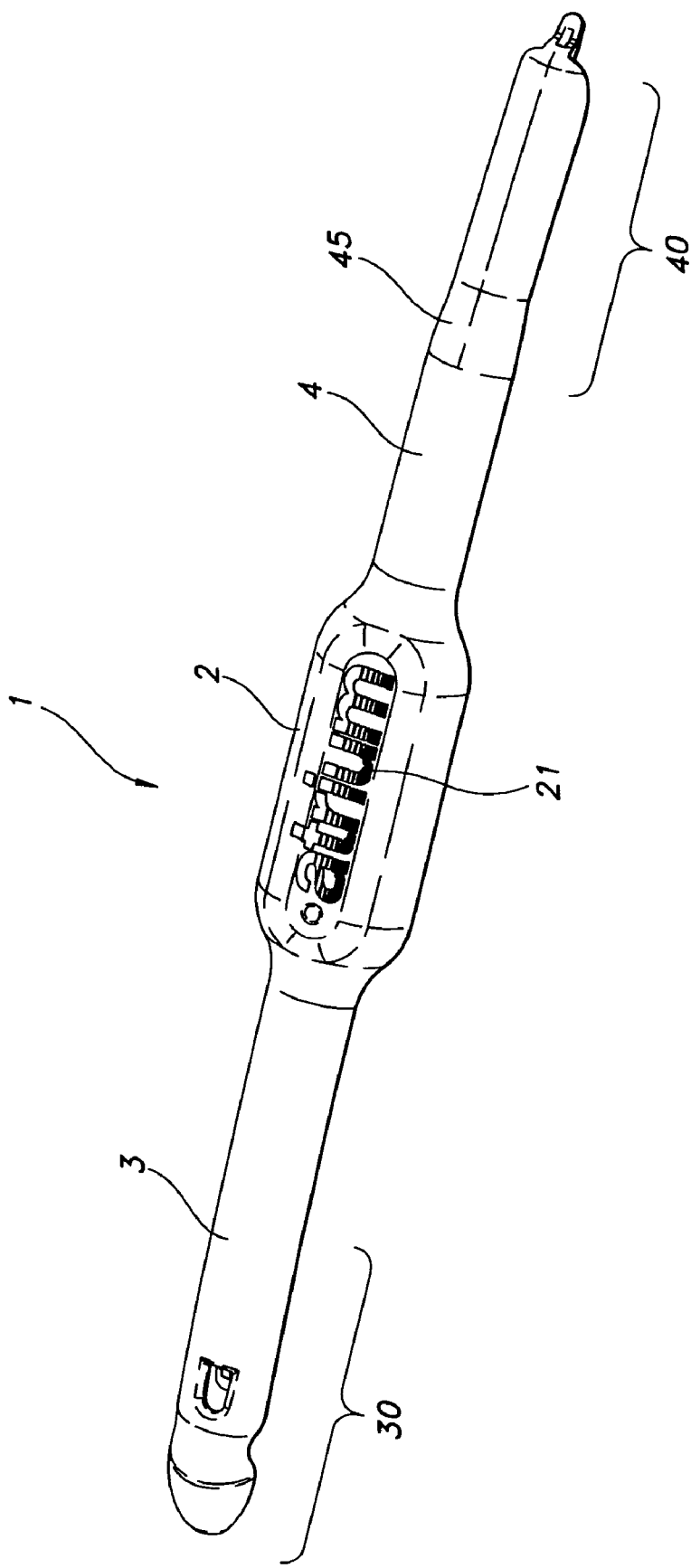
FIG. 1 is a perspective view of an exemplary embodiment of an apparatus for introducing a catheter through a body opening according to aspects of the present invention.

Exemplary aspects of the invention will now be described with reference to embodiments selected for illustration in the drawing. It will be appreciated that this invention is not limited to the embodiments selected for illustration and that various modifications can be made without departing from the spirit or scope of the invention.

Referring generally to the drawing, an apparatus designated 1 is provided for introducing a catheter 50 through a body opening 60 along an insertion axis 7. The apparatus 1 includes an arm 3,4 having an end portion 30,40 configured to extend into the body opening 60 along the insertion axis 7, wherein the arm 3,4 is configured to extend adjacent an external catheter surface. The apparatus 1 also includes a surface 32,42 extending from the end portion 30,40 of the arm 3,4 at an angle to the insertion axis 7, wherein the surface 32,42 is configured to extend at least partially within an aperture 51 formed in the catheter 50.

A method for introducing a catheter 50 into a body opening 60 is also provided. The method includes inserting a surface 32,42 of an introducer 1 at least partially within an aperture 51 formed in an end portion of a catheter 50, thereby engaging the catheter 50. The method also includes advancing the introducer 1 into the body opening 60, thereby applying tension to the catheter 50 to introduce the catheter 50 at least partially into the body opening 60.

FIGS. 1 through 9 show an exemplary apparatus 1 for introducing a catheter 50, shown in FIGS. 10A-12 and described hereafter, through a body opening 60, shown in FIGS. 11 and 12 and described hereafter, according to aspects of the present invention. Apparatus 1 comprises a hub or handle or grip portion 2 with two shafts or arms 3,4 extending from grip portion 2 in opposing directions. The arms 3,4 terminate in a first end portion 30 and a second end portion 40, respectively. While plural arms 3,4 are shown, it is contemplated that only one of arms 3,4 need be provided.

The introducer 1 may be formed from a variety of materials and formed using a variety of forming methods. While a variety of biocompatible materials and suitable manufacturing methods are contemplated within the scope of the invention, exemplary apparatus 1 comprises a plastic material such as medical grade nylon. To provide stiffness to the catheter with which it is used, the exemplary apparatus 1 is formed from a stiff material, and the dimensions of apparatus 1 are selected such that the stiffness of apparatus 1 is greater than that of the catheter.

Exemplary apparatus 1 is formed by a process such as injection molding. Other materials and forming processes can be selected to meet design and manufacturing preference. For example, the apparatus is optimally formed from metal or other non-plastic materials. Additionally, apparatus 1 can be stamped, bent, vacuum formed, or otherwise formed depending upon the material selected and manufacturing preferences.

Grip portion 2 is sized and configured to provide a good gripping surface, so that a surgeon can hold and manipulate apparatus 1 and receive positional feedback. Grip portion 2 has a generally half-round shape, with a greater width than arms 3,4. A textured grip 21 comprising raised ribs or another form of textured surface is optionally provided on the top of the grip portion 2. Textured grip 21 may be formed in the shape of letters to provide a trade name or other identifying indicia, as shown in FIG. 1. Textured grip 21 may be formed on a flattened area on the generally half-round grip portion 2. Textured grip 21 may be formed in a molding die as an integral component of apparatus 1. Alternatively, textured grip 21 can be molded separately and incorporated into apparatus 1. Also, grip 21 is optionally eliminated in favor of a continuous arm structure.

Arms 3,4 extend from grip portion 2 in opposite directions in the exemplary embodiment. As shown in FIG. 1, they are elongated and have a generally half-round cross-sectional shape. Arms 3,4 are configured to provide or increase stiffness for introducing a catheter. A system comprising a catheter (FIGS. 10A and 10B) and apparatus 1 can be inserted at least partially into a body opening (FIGS. 11 and 12) by advancing the catheter system along an insertion axis (FIG. 11) in an insertion direction (FIG. 11).

Each arm 3,4 may be of generally uniform width along its length as shown in arm 3 in FIG. 1, or may optionally have a taper 45 as shown on arm 4 in FIG. 1. Configurations having only one arm are also contemplated within the scope of the invention.

Figure 2:
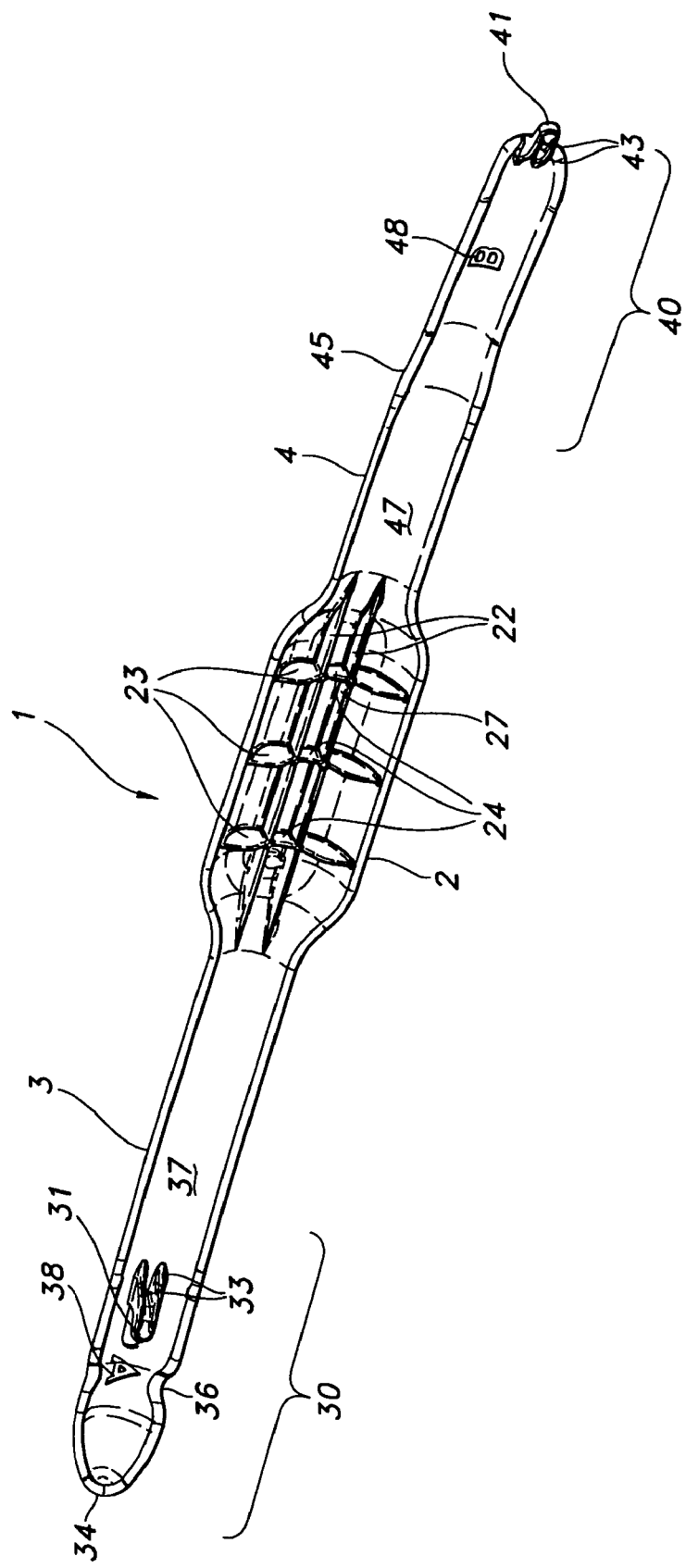
FIG. 2 is a perspective view of the exemplary apparatus of FIG. 1 from its opposite side.

As shown in FIG. 2, apparatus 1 has a generally uniform wall thickness. Opposite the half round shapes described above, grip portion 2 and arms 3,4 form concavities 27,37,47, respectively. Such concavities 27,37,47 are positioned and sized to at least partially receive an outer wall portion of the catheter 50. Accordingly, the apparatus 1 partially surrounds the catheter 50. Such a concave configuration makes it possible to support the catheter 50 against surfaces of the introducer or apparatus 1. The support provided by the apparatus 1 reduces the tendency of the catheter 50 to buckle and helps the user to guide the catheter 50 through the body opening 60.

Also, such a concave configuration makes it possible to reduce the overall profile of the system formed by the catheter 50 and the apparatus 1. A reduced profile makes it possible to insert the catheter 50 and apparatus 1 through a smaller incision (if an incision is provided for body access) or a smaller orifice (if an orifice is employed for body access).

Grip portion 2 has longitudinal stiffening ribs 22 and transverse stiffening ribs 23 to provide enhanced structural stability and stiffness where apparatus 1 is designed to be gripped and manipulated. Longitudinal stiffening ribs 22 extend only to the bottom of the concavities 37,47 in arms 3,4 in the exemplary embodiment shown in FIG. 2. Such a relationship between the ribs 22 and the concavities 37,47 provides a substantially continuous, concave support system against which an outer surface of the catheter 50 rests or is held during insertion.

Transverse stiffening ribs 23 are each preferably formed with a nesting contour 24 configured to conform to the outside surface of a catheter when it is positioned against apparatus 1. Like the ribs 22, nesting contours 24 of ribs 23 cooperate with the concavities 37,47 in arms 3,4 to provide a substantially continuous, concave support against which an outer surface of the catheter 50 rests or is held during insertion.

Thus, a catheter can be positioned with a portion of its external surface received within concavities 37,47 in arms 3,4 and within nesting contour 24 of transverse stiffening ribs 23. Positioning a catheter partially within apparatus 1 provides a low-profile catheter system that does not require significant widening of a body opening to insert the catheter through the body opening.

Also, nesting the catheter in the grip portion 2 of the apparatus allows a surgeon or other medical professional to hold the catheter and apparatus together with his or her hand to enhance manipulation of the catheter system during insertion. Accordingly, improved guidance and alignment of the catheter as it enters the body opening can be achieved.

Figure 3:
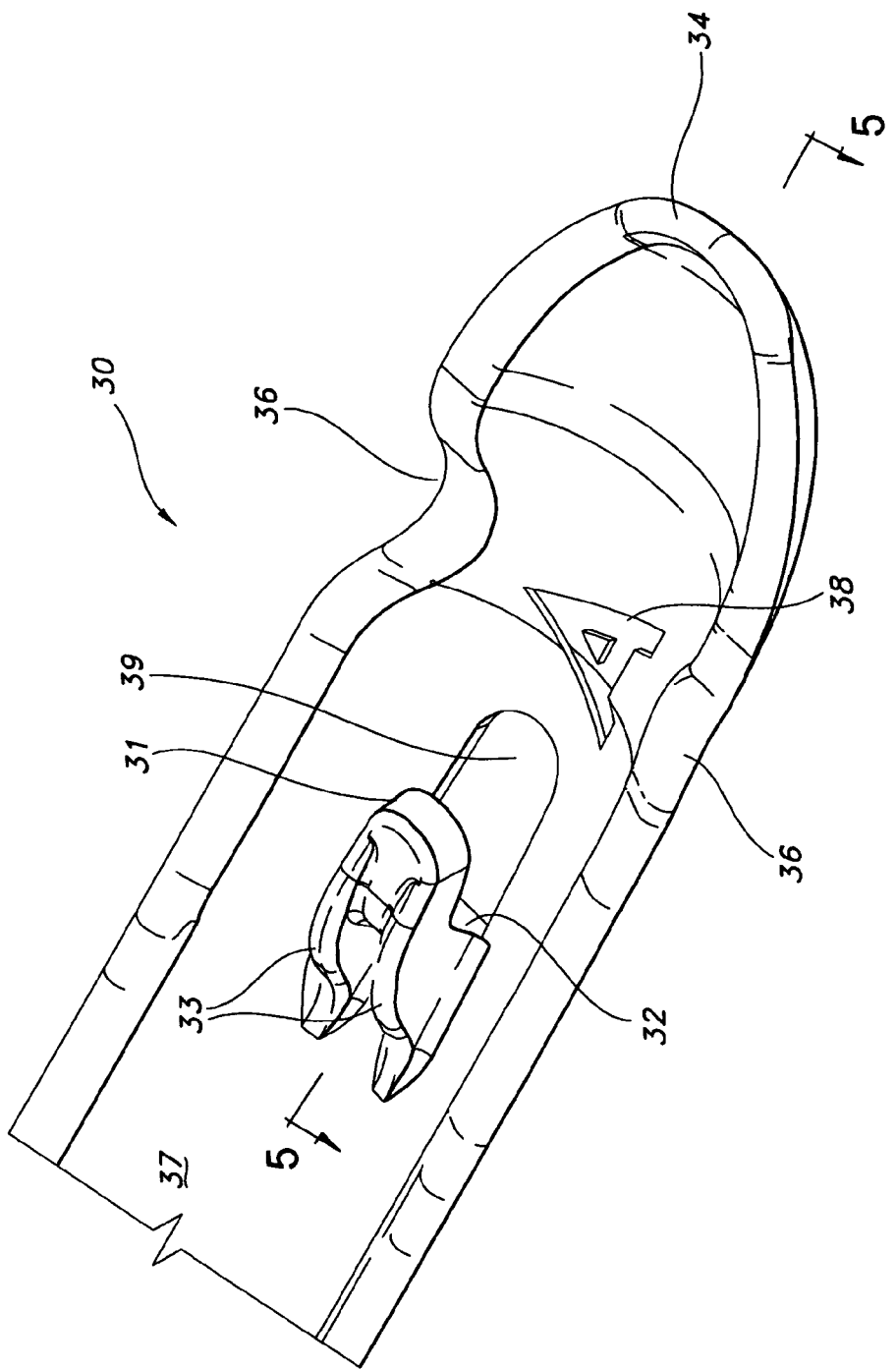
FIG. 3 is a detailed perspective view of a first end portion of the exemplary apparatus of FIGS. 1 and 2.
Figure 4:
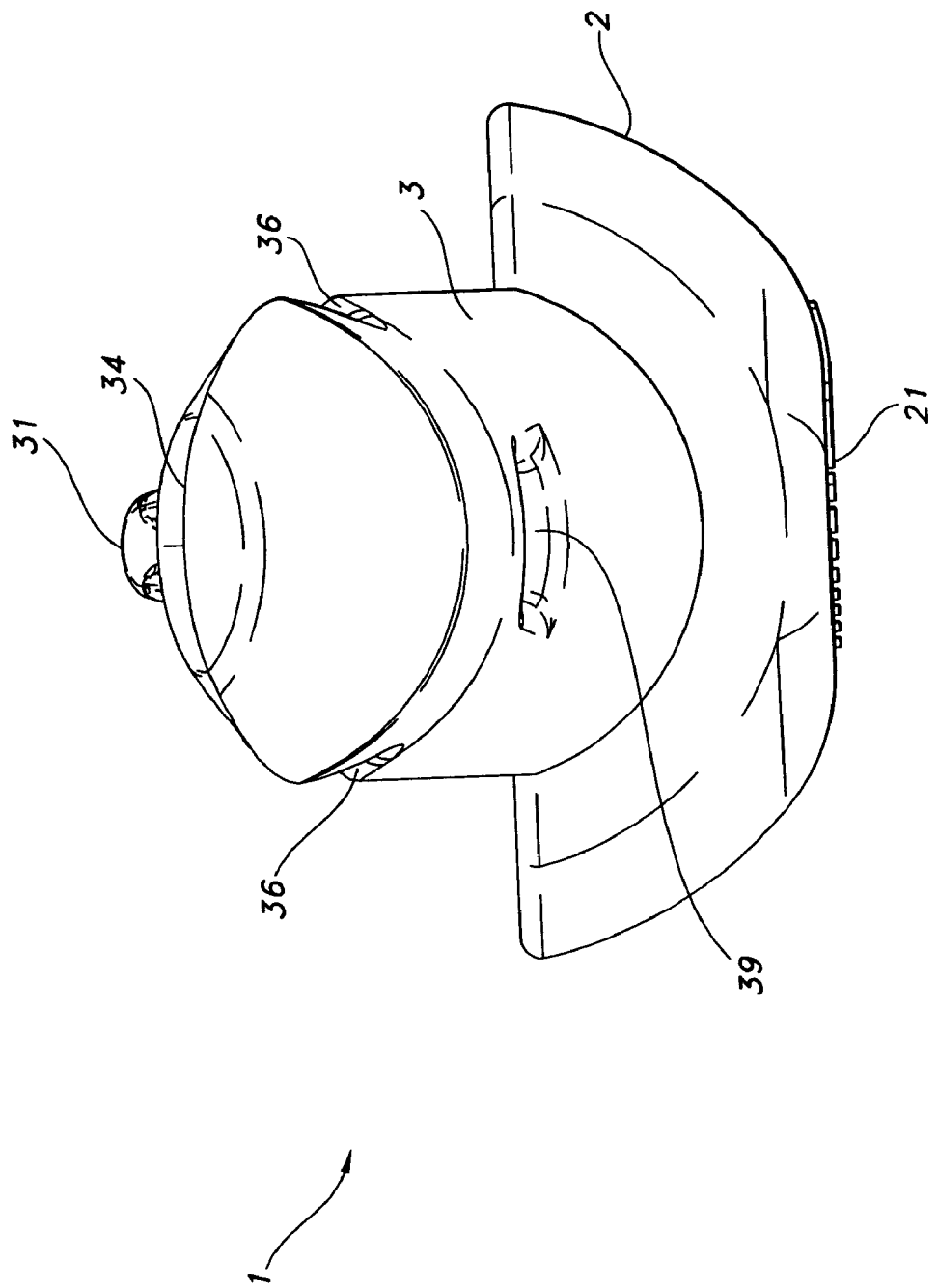
FIG. 4 is an end view of the exemplary apparatus of FIGS. 1 and 2, from the first end.
Figure 5:
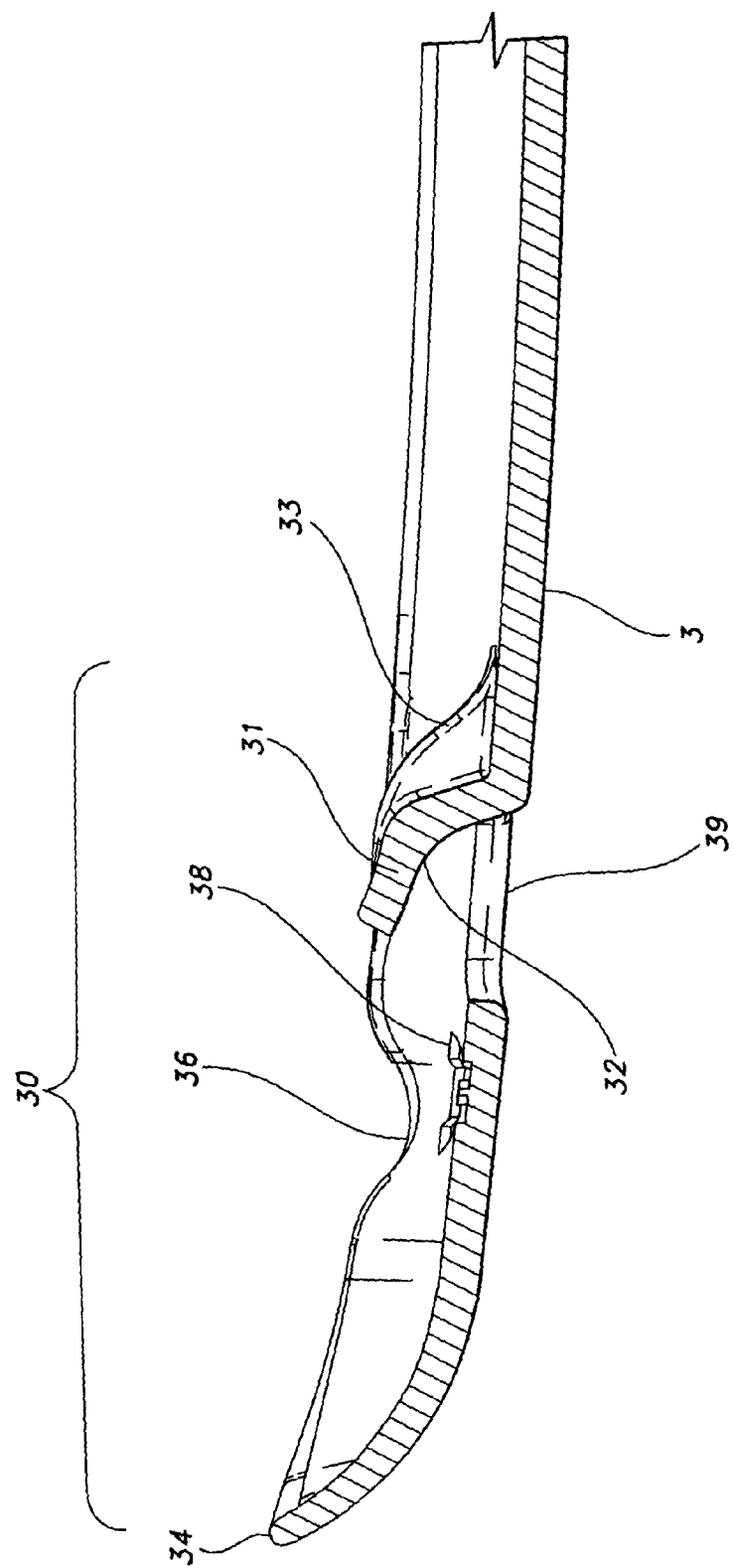
FIG. 5 is a cross-sectional side view of the first end portion of FIG. 3 taken generally along axis 5-5, shown in FIG. 3.

First end portion 30 is shown generally in FIGS. 1 and 2, and in detail in FIGS. 3 through 5. A protrusion in the form of a tang or tab 31 is provided at first end portion 30 of arm 3. Tab 31 is configured to extend at least partially into an aperture (such as eyelet 51 shown in FIGS. 10A and 10B) formed in a catheter (such as catheter 50 shown in FIGS. 10A and 10B). Tab 31 is configured as a projection or protrusion that extends from first end portion 30 of arm 3 at an angle to the insertion axis (FIG. 11). Tab 31 extends radially inwardly from end portion 30 (i.e., into concavity 37) and away from grip portion 2 to form a hook or projection pointing in or along the insertion direction (designated as 8 in FIG. 11).

Gussets 33 may be provided to stiffen and strengthen tab 31. To accommodate an injection molding process for forming tab 31, a slide opening 39 may be provided in first end portion 30 of arm 3 adjacent tab 31. Tab 31 is sized to fit into an aperture (such as the aperture 51 shown in FIGS. 10A and 10B) formed in a catheter (such as the catheter 50 shown in FIGS. 10A and 10B) to be inserted in a body opening (such as opening 60 shown in FIG. 11) of a patient. Tab 31 is optionally formed with a curve that is sized and shaped to engage the aperture in the catheter. A surface 32 of tab 31 is configured to engage the wall of an aperture or other surface formed in the catheter. Surface 32 transfers force from apparatus 1 to the catheter to apply tension to the catheter, thereby advancing the catheter into the body opening.

Indicia 38 are provided on first end portion 30 of arm 3, proximal tab 31. Indicia 38 may be a molded letter, identifying first end portion 30 for visual cross-reference in surgical instructions, or some other selected symbol. For example, instructions may indicate that the surgeon should engage tab A in the last aperture in the catheter to indicate that tab 31, proximal the indicia 38 (having the form of the letter "A"), is to be engaged in the indicated aperture of the catheter.

Although not shown, the configuration of apparatus 1 can provide depth information. Specifically, depth/guidance indications can be provided by the position of the grip for a visual estimation of depth, distance and position of the catheter tip.

First end portion 30 extends past tab 31 and forms a 'cobra head' configuration for at least partially shielding or protecting the end of the catheter and assisting in penetrating the body opening. The 'cobra head' comprises a sharp edge 34, which is rounded to separate the tissue at the body opening when apparatus 1 is advanced along the insertion axis in the insertion direction. Though edge 34 need not be sharp enough to cut tissue, edge 34 may optionally be provided with a blade surface sufficient to cut tissue.

The 'cobra head' can help facilitate the advancement of the apparatus 1 through one or more layers of tissue. For example, when the catheter needs to be advanced through slits formed in multiple tissue layers, the leading end of the apparatus 1 helps to align those slits to reduce the need for additional cutting or dissection.

Also, the leading end of the apparatus 1 can be rotated during insertion to create or enlarge an incision. This allows the user to dissect tissue to enlarge an existing incision as the catheter is being advanced. Accordingly, the configuration of the leading edge of the apparatus 1 can eliminate the need to withdraw the catheter, enlarge the incision with another instrument, and re-inserting the catheter.

First end portion 30 curves from sharp edge 34 to the half-round shape of arm 3, partially covering or shielding the front edge of the catheter and the eyelets when the catheter is engaged on tab 31. Thus the leading edge 34 separates the tissue before the catheter is advanced through the body opening. A notch 36 may be formed in the sides of first end portion 30 to provide flexibility to the 'cobra head' for easier insertion of the catheter assembly. Alternatively, to provide a smooth surface and perhaps greater rigidity, the notches 36 forming the 'cobra head' can optionally be eliminated.

Figure 6:
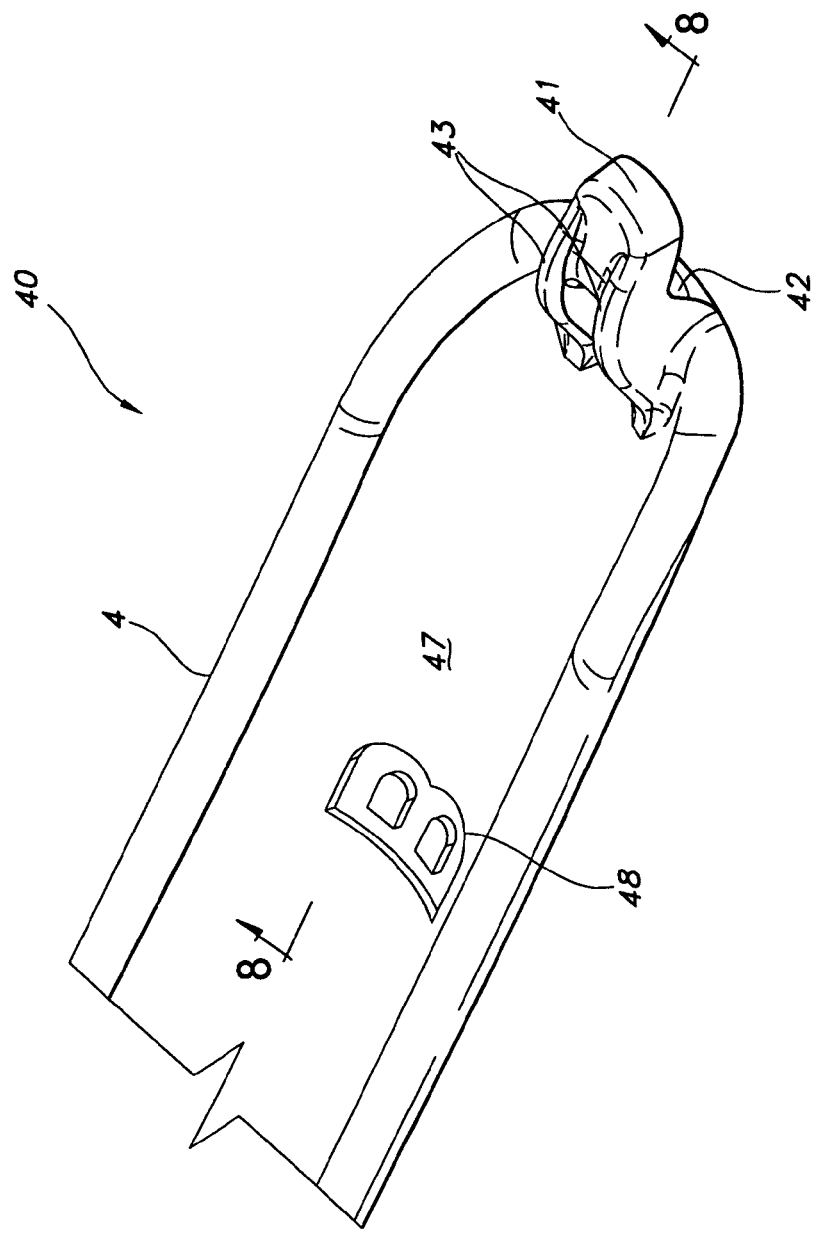
FIG. 6 is a detailed perspective view of a second end portion of the exemplary apparatus of FIGS. 1 and 2.
Figure 7:
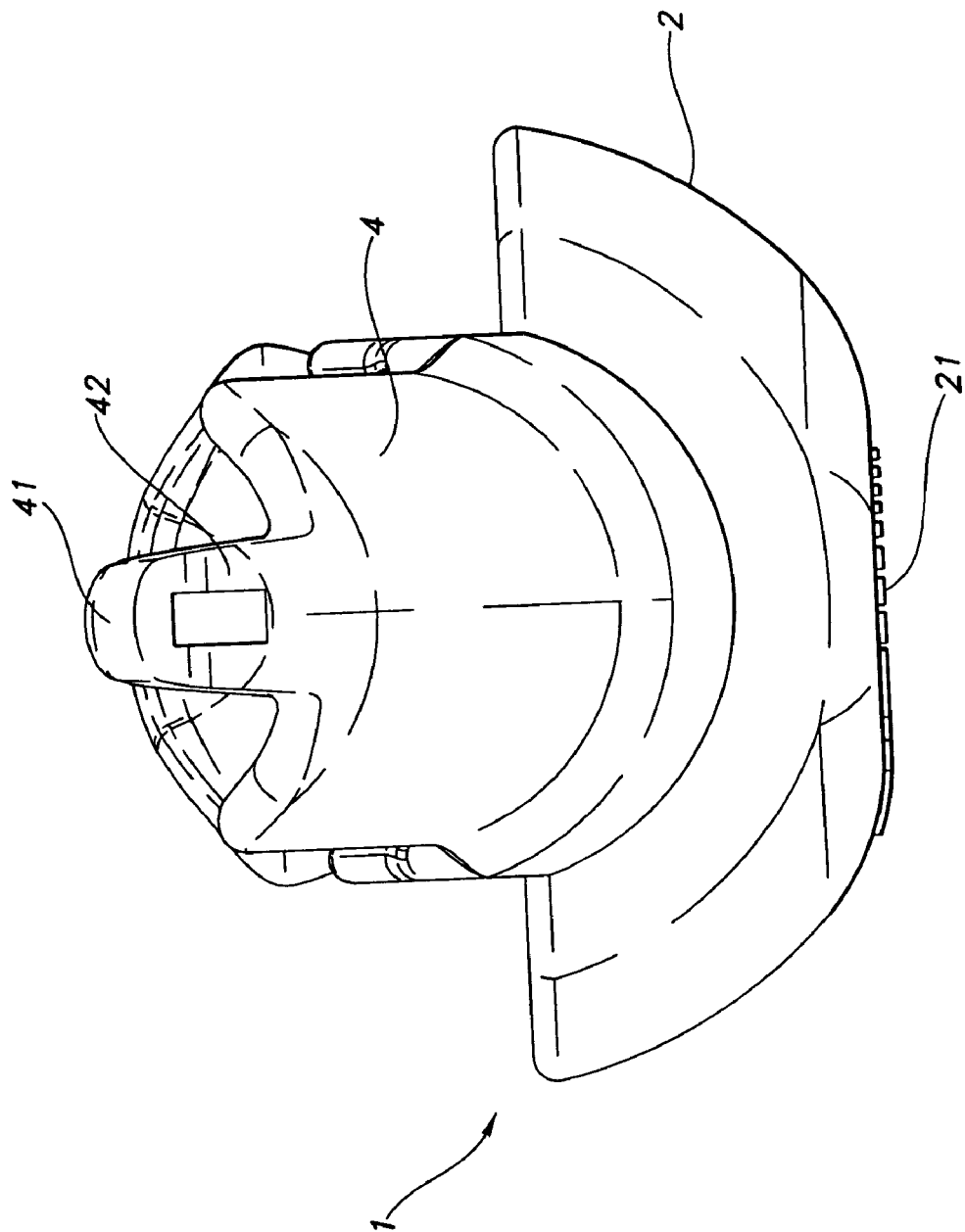
FIG. 7 is an end view of the exemplary apparatus of FIGS. 1 and 2, from the second end.
Figure 8:
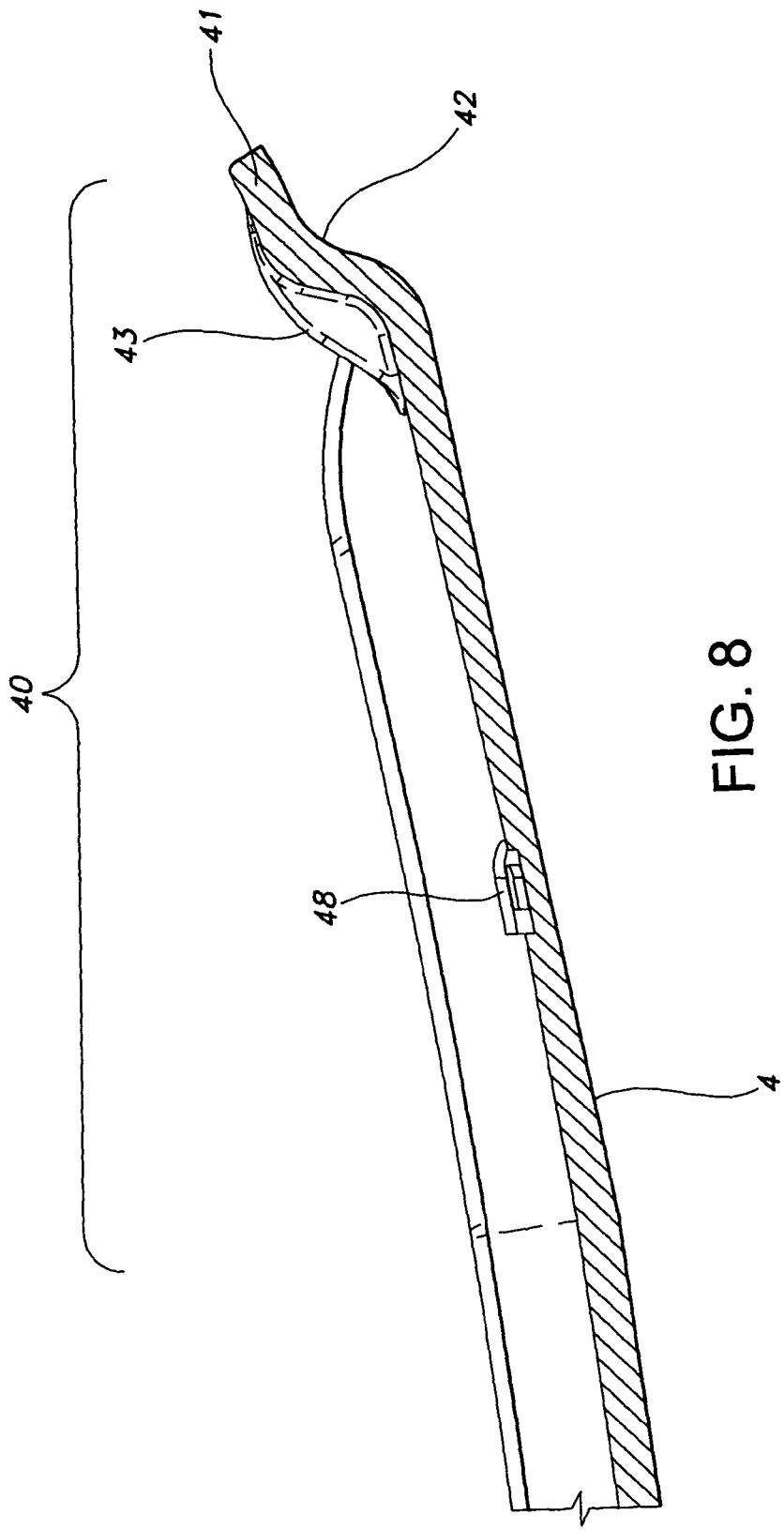
FIG. 8 is a cross-sectional side view of the second end portion of FIG. 6 taken generally along axis 8-8, shown in FIG. 6.

Second end portion 40 is shown in FIGS. 1 and 2, and in greater detail in FIGS. 6 through 8. Like first end portion 30, second end portion 40 has a tab 41 extending from the second end portion 40 of arm 4. Tab 41, however, extends longitudinally past the terminal end of arm 4. Tab 41 extends from second end portion 40 of arm 4 at an angle to the insertion axis (FIG. 11). Tab 41 extends radially inwardly from second end portion 40 (i.e., toward concavity 47) and away from grip portion 2 to form a hook or projection pointing in or along the insertion direction (FIG. 11).

Gussets 43 may be provided to stiffen and strengthen tab 41. Because tab 41 extends past arm 4, a slide opening is not required in end portion 40. Tab 41 is sized to fit into an aperture (FIGS. 10A and 10B) formed in a catheter (FIGS. 10A and 10B) to be inserted in a body opening (FIG. 11) of a patient. Tab 41 is preferably formed with a curve that is sized and shaped to engage the aperture in the catheter. A surface 42 of tab 41 is configured to engage the wall of an aperture formed in the catheter. Specifically, surface 42 extends at an angle to the insertion axis 7. Surface 42 transfers force from apparatus 1 to the catheter to apply tension to the catheter, thereby advancing the catheter into the body opening.

Indicia 48 are provided on second end 40 of arm 4, proximal tab 41. For example, indicia 48 may be a molded letter, different from the letter of indicia 38, identifying second end 40 for visual cross-reference in surgical instructions.

The insertion direction for arm 4 is opposite the insertion direction for arm 3. In other words, apparatus 1 could be placed in one of two opposing orientations depending upon which of arms 3,4 is to be used to insert a catheter into a body opening, depending upon the preference of the user and/or the configuration of the catheter and the body opening through which the catheter is to be inserted.

Specifically, a particular surgeon or medical professional may prefer to use arm 3 to introduce a catheter to enjoy the benefit of the leading end of the end portion 30 of the arm 3, which provides a shield and support for the end of the catheter as well as a tool for expanding the body opening or dissecting tissue. Alternatively, a particular surgeon or medical professional may prefer to use arm 4 to introduce a catheter to enjoy the benefit of the leading end of the catheter, which provides a flexible surface for introduction through the body opening. Also, a particular surgeon or medical professional may prefer to use one end portion 30 for some procedures and catheter sizes.

Figure 9:
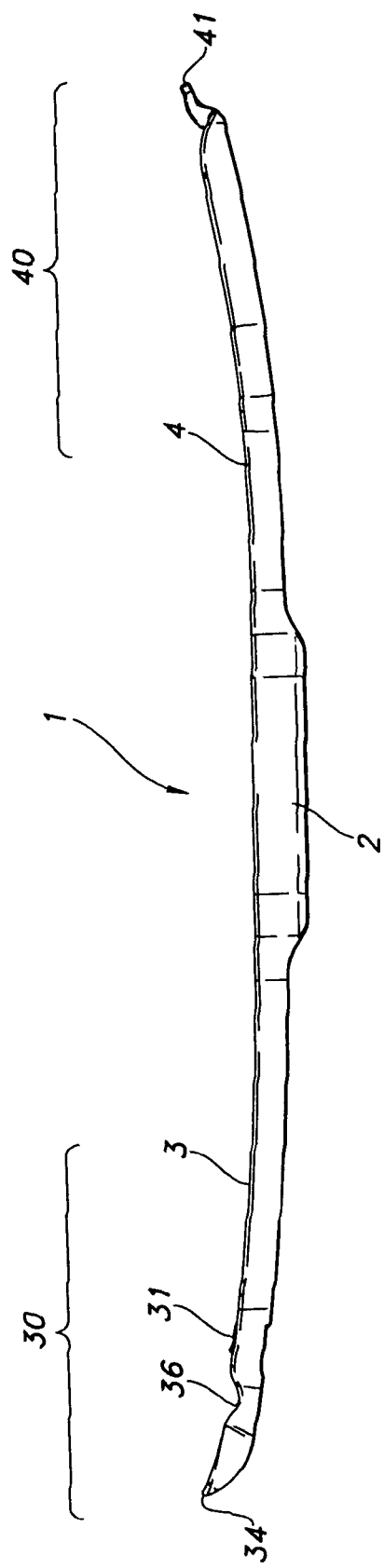
FIG. 9 is a side view of the exemplary apparatus of FIG. 1.

As shown in FIG. 9, apparatus 1 can be curved along its longitudinal length to facilitate insertion of a catheter into a body opening, and to provide additional stiffness to apparatus 1. While a concave curvature is shown between first end 31 and second end 41, other curvatures (or a straight configuration) are contemplated within the scope of the invention.

A method for introducing a catheter 50 into a body opening 60 is shown in FIGS. 10A through 12. In an exemplary embodiment of the method illustrated in FIG. 10B, tab 41 projecting from second end portion 40 of apparatus 1 is engaged with an eyelet or aperture 51 of the catheter 50 and introduced with catheter 50 into body opening 60. Catheter 50 is a generally flexible tubular body having a lumen extending longitudinally through the catheter 50. One or more apertures 51 are formed in catheter 50 near the end to be introduced into a patient's body.

As shown in FIG. 10B, a surface 42 of tab 41 extending from second end portion 40 of an introducer apparatus 1 is inserted into an aperture 51 formed in catheter 50. To insert the surface 42, apparatus 1 is positioned at an angle to catheter 50. Surface 42 of tab 41 is then guided into aperture 51. When surface 42 extends into aperture 51, apparatus 1 is pivoted so that arm 4 extends adjacent a portion of the external surface of catheter 50, with surface 42 engaging the wall of aperture 51 in catheter 50 and forming a second catheter system 6.

As shown in FIG. 11, a surgeon grasps second catheter system 6 at grip portion 2 of apparatus 1. Catheter system 6 comprises apparatus 1 and catheter 50 partially received in concavity 47 and nesting contours 24 of apparatus 1. The surgeon then advances second catheter system 6 into the body opening 60 along insertion axis 7 in insertion direction 8. Body opening 60 may be, for example, a surgical incision for draining fluid or injecting fluid into a body cavity. Alternatively, body opening 60 may be a natural body orifice.

Figure 14:
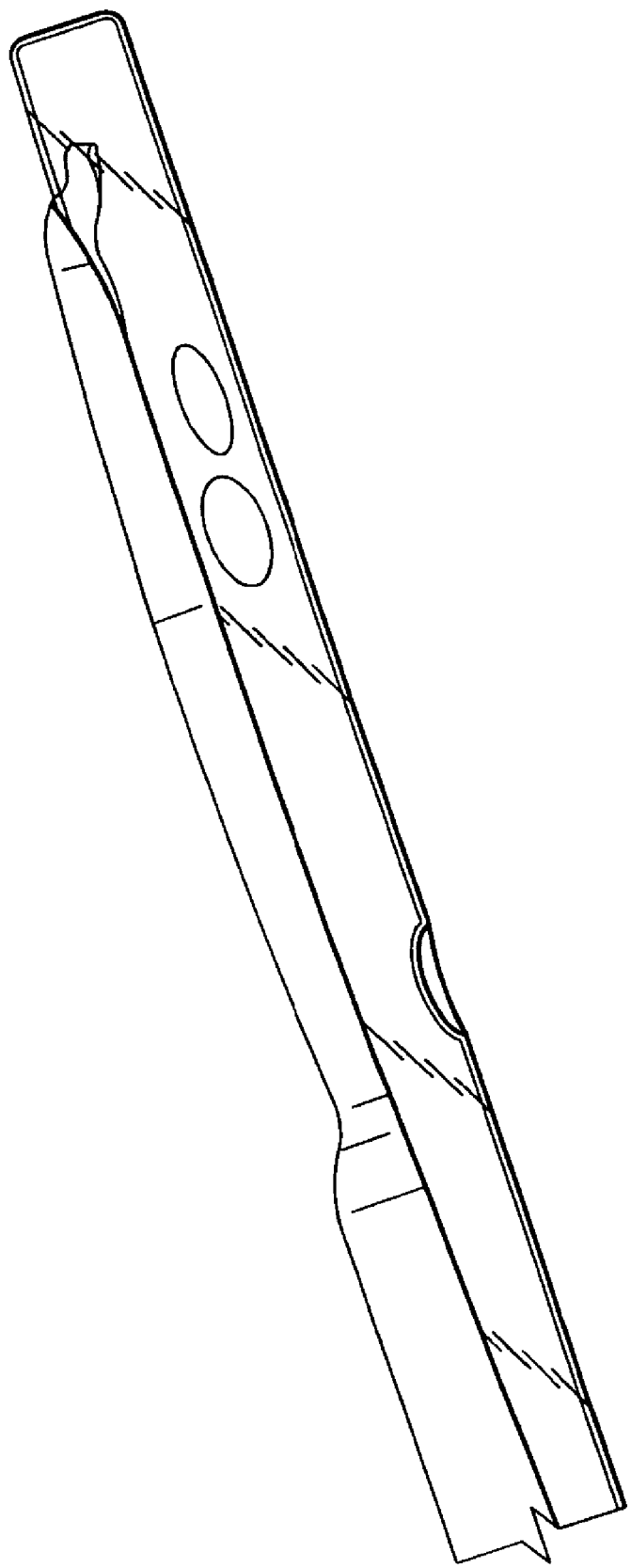
FIG. 14 shows an alternate exemplary catheter system for introducing a catheter into a body opening according to aspects of the invention.

As shown in FIGS. 11 and 14, catheter system 6 is configured so that catheter 50 extends beyond apparatus 1. Therefore, the leading end of catheter 50 is introduced into body opening 60 before apparatus 1. Only the small portion of catheter 50 beyond aperture 51 is introduced into body opening 60 before apparatus 1. Because this portion is small (less than about one half inch, for example) it is not very susceptible to bending or collapsing or buckling. Apparatus 1 supports the portion of catheter 50 trailing aperture 51. Since apparatus 1 has good stiffness, it transfers force from the apparatus 1 and to the catheter 50 at aperture 51. Thus, apparatus 1 applies tension on catheter 50 to introduce the catheter into the body opening 60.

In effect, the catheter 50 is pulled into the body opening 60 by the force transferred from the apparatus 1 to the leading end of catheter 50. Accordingly, the strength of the catheter in tension is used to introduce the catheter as opposed to its weakness and tendency to buckle in compression. This may be especially beneficial for soft catheters such as thoracic drainage catheters formed from silicone.

Figure 13:
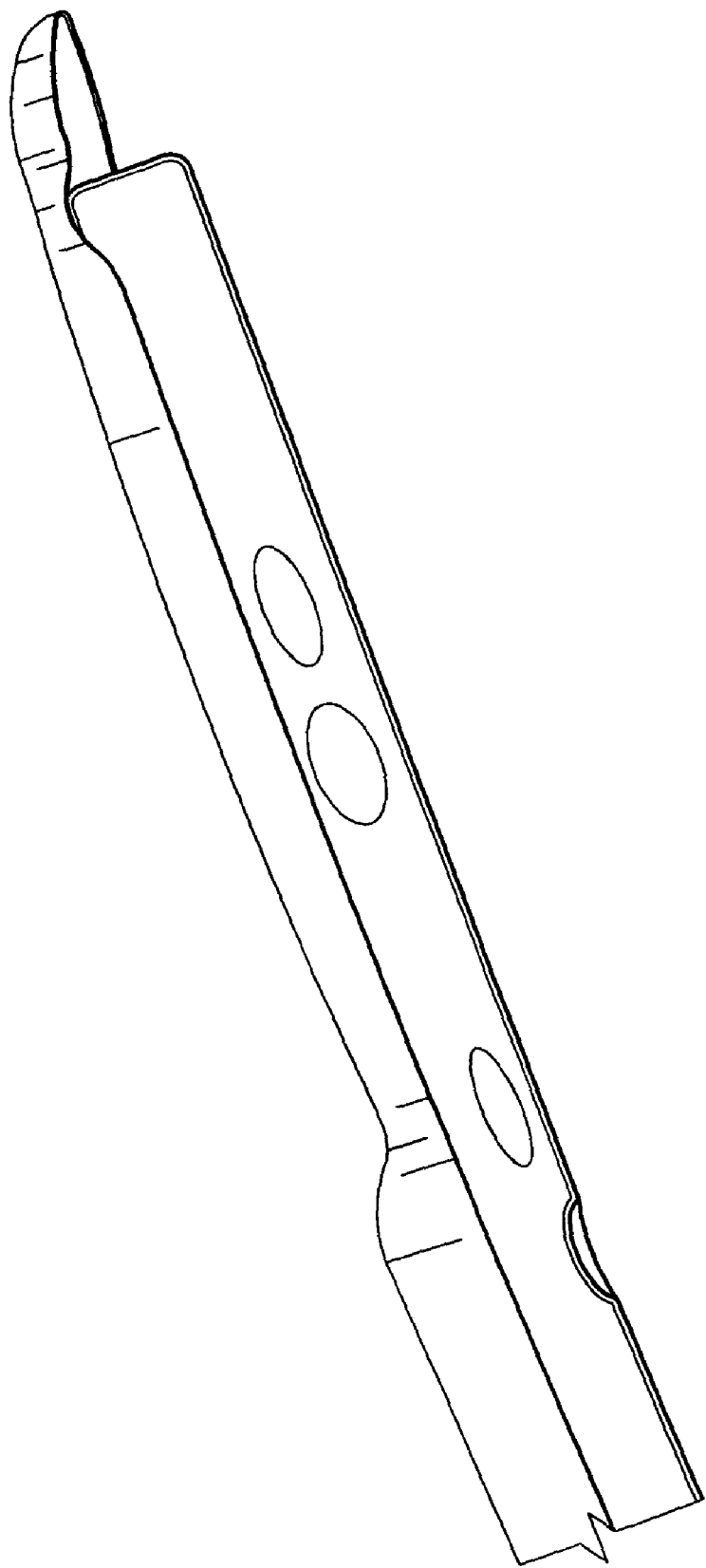
FIG. 13 shows an exemplary catheter system for introducing a catheter into a body opening according to aspects of the invention.

Alternatively, tab 31 projecting from first end portion 30 of apparatus 1 is engaged with catheter 50 and introduced with catheter 50 into body opening 60. As shown in FIG. 10A, a surface 32 extending from first end portion 30 of an introducer apparatus 1 is inserted into an aperture 51 formed in catheter 50. To insert the surface 32, apparatus 1 is positioned at an angle to catheter 50. Surface 32 of tab 31 is then guided into aperture 51. When surface 32 extends into aperture 51, apparatus 1 is pivoted so that arm 3 extends adjacent a portion of the external surface of catheter 50, with surface 32 engaging the wall of aperture 51 in catheter 50 and forming a first catheter system 5 as shown in FIG. 13.

First catheter system 5 is then advanced into body opening 60. As described above, in first catheter system 5, the 'cobra head'0 of first end portion 30 extends past the end of catheter 50 partially shielding the end of catheter 50. Sharp edge 34 parts tissue at body opening 60, thereby facilitating the advance of first catheter system 5.

Because apparatus 1 extends external catheter 50, introducer apparatus 1 does not block a fluid path inside catheter 50. This provides at least two advantages. First, fluid can be drained or introduced substantially immediately upon positioning catheter 50, rather than being delayed by removal of an internal trocar or internal introducer. Second, a collection device may be attached to catheter 50 during insertion, so that potentially bio-hazardous fluids are contained.

Following insertion of either first catheter system 5 or second catheter system 6, the apparatus 1 may be removed as shown in FIG. 12 by withdrawing apparatus 1 in a second direction 9, opposite insertion direction 8. Catheter 50 may be restrained from external the body, such as by the surgeon's hand, and apparatus 1 may be withdrawn from the body opening 60. Because tabs 31,41 are angled in the insertion direction 8, they slide out of aperture 51 when apparatus 1 is withdrawn and catheter 50 is restrained. Thus, the introducer apparatus 1 may be removed without disturbing the positioning of catheter 50.

Figure 15:
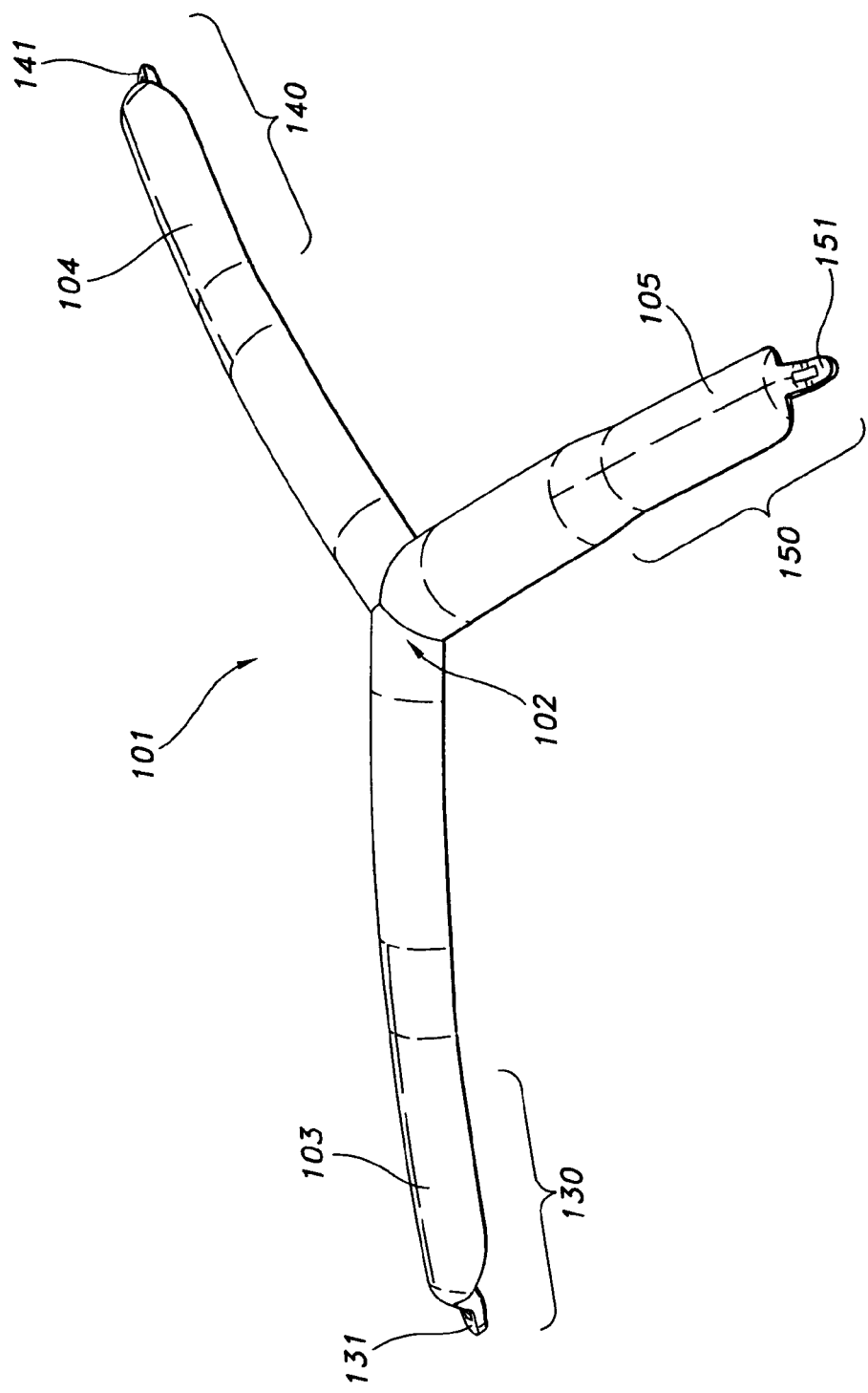
FIG. 15 is a perspective view of another exemplary embodiment of an apparatus for introducing a catheter through a body opening according to aspects of the present invention.
Figure 16:
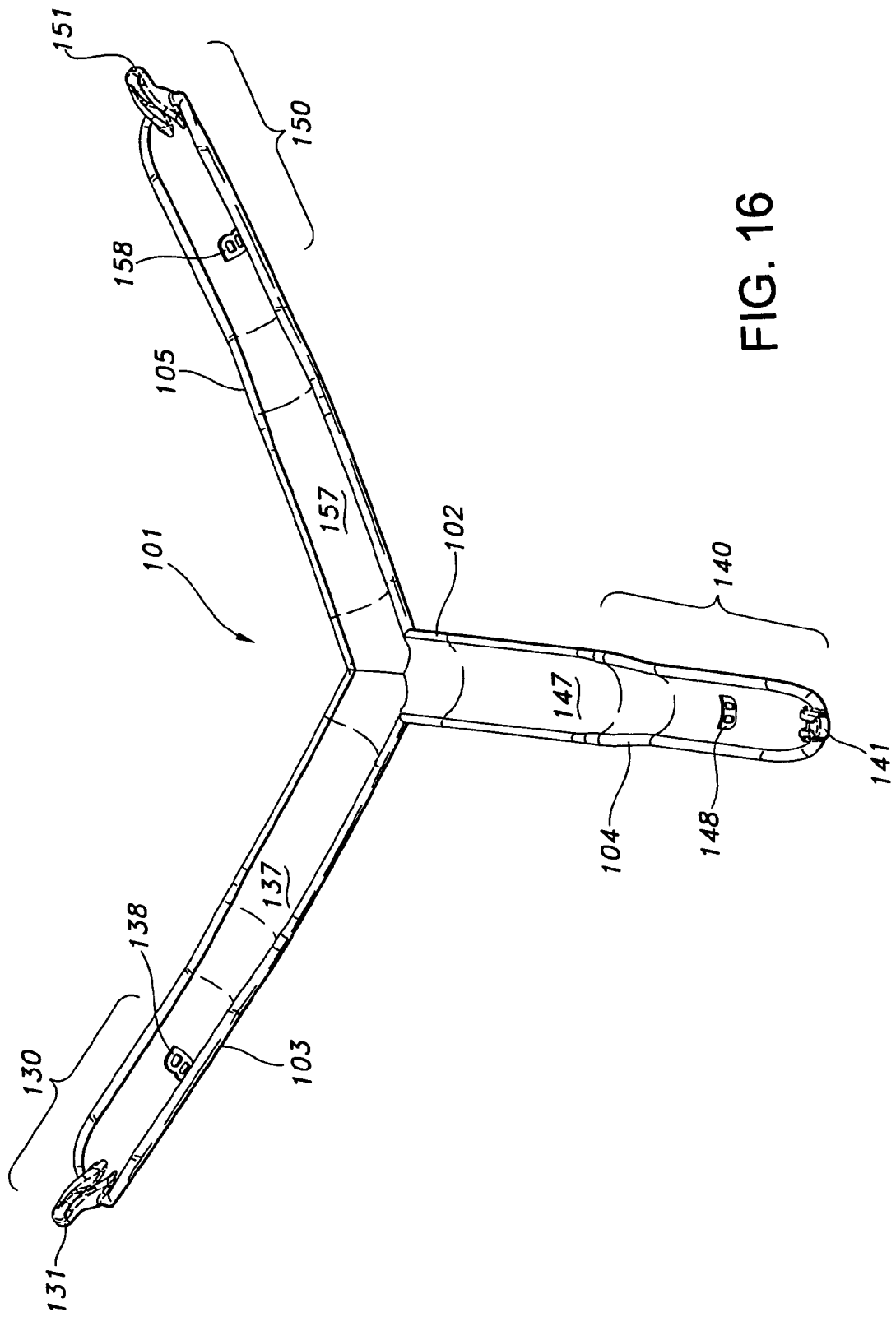
FIG. 16 is a perspective view of the exemplary apparatus of FIG. 15 from its opposite side.

Referring now to FIGS. 15 and 16, yet another exemplary embodiment of an apparatus (generally designated by the numeral 101) is shown. Apparatus 101 differs from apparatus 1 in that it includes three (3) arms 103,104,105, each having respective end portions 130,140,150 and engagement tabs 131,141,151. Apparatus 101 is similar to apparatus 1, however, in that the construction of each of the arms 103,104,105 and respective tabs 131,141,151 is generally the same as arm 4 and tab 41 of apparatus 1.

Referring specifically to FIG. 15, apparatus 101 comprises a hub or handle or grip portion 102 with three (3) shafts or arms 103,104,105 extending from grip portion 102 in opposing directions. The arms 103,104,105 are optionally separated evenly (i.e., by 120°), though other angles are contemplated as well. The grip portion 102 optionally can be modified to conform to grip portion 2 of apparatus 1. For example, an enlarged hub area can be provided for additional grip surface area, and a grip surface like surface 21 can be added.

The arms 103,104,105 of apparatus 101 terminate in a first end portion 130, a second end portion 140, and a third end portion 150, respectively. As mentioned previously, while plural arms 103,104,105 are shown, it is contemplated that an apparatus having one arm, two arms, or four or more arms can be selected as well according to this invention.

As shown in FIG. 16, apparatus 101 has a generally uniform wall thickness like that of apparatus 1. Arms 103,104, 105 form concavities 137,147, 157, respectively. Like concavities 37,47 of apparatus 1, such concavities 137,147,157 are positioned and sized to at least partially receive an outer wall portion of the catheter 50. Accordingly, like apparatus 1, the apparatus 101 partially surrounds the catheter 50.

Each of the tips 131,141,151 of the end portions 130,140, 150 of arms 103,104,105, respectively, is substantially the same in the exemplary apparatus 101. Nevertheless, two or more or all of end portions 130,140,150 may differ from one another in size (e.g., to accommodate a different catheter size or to facilitate a different procedure) and/or tip configuration (e.g., to accommodate a user's tip preference or to facilitate a different procedure). For example, one or more of arms 103, 104,105 can have a tip similar to tip 31 of end portion 30 of apparatus 1. Indicia, such as indicia 138,148,158 are optionally provided to serve the same function as indicia 38,48 of apparatus 1.

In use, a medical professional selects an end portion from among end portions 130,140,150 of apparatus 101; engages a catheter such as catheter 50 with the tip 131,141,151 of the selected end portion 130,140,150; and introduces the catheter 50 through a body opening such as opening 60. Accordingly, the manner of use of apparatus 101 is substantially the same as for apparatus 1.

Although the invention is illustrated and described herein with reference to specific embodiments, the invention is not intended to be limited to the details shown. Rather, various modifications may be made in the details within the scope and range of equivalents of the claims and without departing from the invention.

For example, exemplary embodiments of this invention may have a single arm, opposing arms, or can even be provided without arms if the grip or handle is sufficient to support catheter-engaging surfaces. Also, although embodiments of the catheter system have been illustrated with use of one end or the other, it is contemplated that both ends of an apparatus can be used in a single procedure.

Also, both ends of the apparatus 1 can be engaged to eyelets of the catheter if the spacing between the eyelets roughly corresponds to the spacing between the tabs 31, 41. As such, the apparatus 1 can be engaged to the catheter as a stiffening member to form a kit. The catheter system can be packaged with the introducer apparatus engaged to the catheter for convenience.

Further, if the apparatus is provided with opposed end portions both configured for catheter engagement and insertion, the end portions can be the same as one another. Alternatively, although it is recognized that the apparatus 1 can be used to introduce a wide range of catheter sizes, they can be different to accommodate different preferences, catheter sizes, body opening types, and other factors. Additional variations can be made to the illustrated embodiments within the spirit and scope of the invention.

What is claimed:

1. An apparatus for introducing a catheter through a body opening along an insertion axis and in an insertion direction, the catheter having an external catheter surface and an aperture defined in a wall of the catheter, said apparatus comprising:

plural arms each having an end portion configured to extend into the body opening in the insertion direction, each said arm being configured to extend adjacent the external catheter surface; and a projection extending from said end portion of each said arm at an angle to said insertion axis and in a direction toward the insertion axis, each said projection being configured to extend at least partially within the aperture defined in the wall of the catheter;

wherein a forward surface of at least one of said projections extends from said end portion of said arm at an acute angle with respect to the insertion axis and along the insertion direction, each said projection being shaped to engage the wall of the catheter and introduce the catheter in the insertion direction;

wherein each of said arms of said apparatus defines a cavity for accommodating a portion of the catheter, said cavity extending along each of said arms of said apparatus;

wherein said projection of at least one of said arms extends from said end portion of said arm at a location that is spaced from an end of said arm;

wherein said projection of at least one of said arms extends beyond the end of said arm; and wherein a portion of the forward surface of said projection extends from said end portion of said arm in a direction substantially parallel to the insertion axis.

2. The apparatus of claim 1 wherein each said arm of said apparatus is offset from said insertion axis.

3. The apparatus of claim 1 wherein said end of at least one of said arms is configured to extend beyond a leading end of the catheter when the projection of said arm engages the wall of the catheter, thereby shielding the leading end of the catheter as it is introduced into the body opening.

4. The apparatus of claim 1 wherein said end of at least one of said arms is configured to separate tissue as said apparatus is advanced along the insertion axis.

5. The apparatus of claim 1 wherein said projection extending from said end portion of at least one of said arms extends toward the insertion axis and substantially parallel to said insertion direction.

6. The apparatus of claim 1 further comprising a grip portion.

7. An apparatus for introducing a catheter through a body opening along an insertion axis and in an insertion direction, the catheter having an external catheter surface and an aperture defined in a wall of the catheter, said apparatus comprising:

plural arms each having an end configured to extend into the body opening in the insertion direction, each said arm being configured to extend adjacent the external catheter surface, wherein said arm of said apparatus each defines a cavity for accommodating a portion of the catheter, said cavity extending along each said arm of said apparatus;

a first projection extending from said end portion of at least one of said arms at an angle to said insertion axis and in a direction toward the insertion axis, said first projection being configured to extend at least partially within the aperture defined in the wall of the catheter, wherein said first projection extends from said end portion of said arm at a location that is spaced from an end of said arm;

a second projection protruding from said end of at least one of said arms at an acute angle to said insertion axis and in a direction toward the insertion axis, said second projection being configured to extend at least partially within the aperture defined in the wall of the catheter, said second projection extending beyond the end of said arm; and at least one of said projections including a curved or angled surface extending from said end of said arm at an angle to said insertion axis and in a direction toward the insertion axis, said curved or angled surface being shaped to engage an edge surface of the aperture defined in the wall of the catheter and to transfer force from the apparatus to the wall of the catheter upon introducing the catheter through the body opening along the insertion axis.

* * * * *

UNITED STATES PATENT AND TRADEMARK OFFICE
CERTIFICATE OF CORRECTION

| | |
|---|---|
| PATENT NO. | : 7,758,586 B2 |
| APPLICATION NO. | : 10/428981 |
| DATED | : July 20, 2010 |
| INVENTOR(S) | : Rudolph Muto et al. |

It is certified that error appears in the above-identified patent and that said Letters Patent is hereby corrected as shown below:

Under column 10, claim 7, (old claim 38), line 11, "arm" should read --arms--.

Signed and Sealed this
First Day of February, 2011

David J. Kappos
*Director of the United States Patent and Trademark Office*